United States Patent [19]

Kolhouse et al.

[11] Patent Number: 5,559,038

[45] Date of Patent: Sep. 24, 1996

[54] GAS CHROMATOGRAPHY/MASS SPECTROMETRY DETERMINATION OF OXIDIZED SULFHYDRYL AMINO ACIDS

[75] Inventors: J. Fred Kolhouse, Denver; Cheruppolil R. Santhosh-Kumar, Lakewood; John C. Deutsch, Denver, all of Colo.

[73] Assignee: The Regents of the University of Colorado, Boulder, Colo.

[21] Appl. No.: 238,754

[22] Filed: May 4, 1994

[51] Int. Cl.$^6$ ................................................. G01N 30/00
[52] U.S. Cl. ........................... 436/86; 436/120; 436/161; 436/173; 436/174; 436/178
[58] Field of Search ..................... 436/173, 174, 436/178, 161, 86, 120; 95/82

[56] References Cited

U.S. PATENT DOCUMENTS 4,940,658  7/1990  Allen et al. ................................. 435/4

OTHER PUBLICATIONS

Heafield et al. (1990) "Plasma Cysteine and Sulphate Levels in Patients with Motor Neurone, Parkinson's and Alzheimer's Disease", *NeuraSci. Lett.* 110:216–220.

Perry et al. (1991) "Amyotrophic Lateral Sclerosis: Fasting Plasma Levels of Cysteine and Inorganic Sulfate are Normal, as are Brain Contents of Cysteine", *Neurology* 41:487–490.

Cohen et al. (1974) "The Administration of Methionine to Chronic Schizophrenic Patients: A Review of Ten Studies", *Biol. Psychiatry* 8:209–225.

Deutsch et al. (1989) "A 'Glutamatergic Hypothesis' of Schizophrenia Rationale for Pharmacotherapy with Glycine", *Clin. Neuropharmacology* 1(vol.12):1–13.

Olney, J. W. (1989) "Excitatory Amino Acids and Neuropsychiatric Disorders", *Biol. Psychiatry* 26:505–525.

Sharvon et al. (1980) "The Neuropsychiatry of Megaloblastic Anaemia", *Br. Med. J.* 281:1036–1038.

MacKenzie et al., *J. Chromatogr.* vol. 187 No. 1, pp. 239–243 (1980).

Kataoka et al., *J. Chromatogr.* vol. 354 pp. 482–485 (1986).

Ng et al., *J. Chromatogr.* vol. 513 pp. 61–69 (1990).

Santnosh–Kumar et al., *Anal. Biochem*, vol. 220 No. 2 pp. 249–256 (1994).

Grieve and Griffiths (1992) "Simultaneous Measurement by HPLC of the Excitatory Amino Acid Transmitter Candidates Homocysteate and Homocysteine Sulphinate Supports a Predominant Astrocytic Localisation", *Neuroscience Letters* 145:1–5.

Klancnik et al. (1992) "Release of Endogenous Amino Acids, Including Homocysteic Acid and Cysteine Sulphinic Acid, from Rat Hippocampal Slices Evoked by Electrical Stimulation of Schaffer Collateral–Commissural Fibres", *Neuroscience* 49:557–570.

Vahora et al. (1988) "S–Adenosylmethionine in the Treatment of Depression", *Neurosci. & Behavioural Rev*, 12:139–141.

Luchi and De Marco (1972) "Synthesis of Homocysteine-sulfinic Acid", *Anal. Biochem* 45:236–241.

Lipton et al. (1994) "Excitatory Amino Acids as a Final Common Pathway for Neurologic Disorders", *N.E.J. Med.* 330:613–622.

Francis et al. (1989) "Brain Amino Acid Concentrations and $Ca^{2+}$–dependent Release in Intractable Depression Assessed Antemortem", *Brain Res.* 494:315–324.

Ohmori et al. (1972) "Unusual Sulfur–Containing Amino Acids in the Urine of Homocystinuric Patients: III. Homocysteic Acid, Homocysteine Sulfinic Acid, S–(Carboxymethylthio) Homocysteine, and S–(3–Hydroxy–3–Carboxy–n–Propyl) Homocysteine", *Physiol. Chem. & Physics.* 4:286–294.

Perry et al. (1985) "Hallervorden–Spatz Disease: Cysteine Accumulation and Cystein Dioxygenase Deficiency in the Globus Pallidus", *Ann. Neurol.* 18:482–489.

Misra and Olney (1975) "Cysteine Oxidase in Brain", *Brain Res.* 97:117–126.

Mewett et al. (1983) "Pharmacology of the Excitatory Actions of Sulphonic and Sulphinic Amino Acids", in Mandell, P., DeFeudis, F. V. (eds) *CNS Receptors: From Pharmacology to Behaviour*, 163–174, Raven Press, New York.

Deusch, J. C. and Kolhouse, J. F. (1993) "Ascorbate and Dehydroascorbate Measurements in Aqueous Solutions and Plasma Determined by Gas Chromatography—Mass Spectrometry", *Anal. Chem.* 65:321–326.

Do et al. (1986) "In Vitro Release of Endogenous Excitatory Sulfur–Containing Amino Acids from Various Rat Brain Regions", *J. Neurochem.* 46:779–786.

Griffiths, R. (1993) "The Biochemistry and Pharmacology of Excitatory Sulphur–Containing Amino Acids", *Biochem. Soc. Trans.* 21:66–72.

Mudd et al. (1989) "The Metabolic Basis of Inherited Disease", in Scriver, C. R. et al. (eds) *Disorders of Transsulfuration*, pp. 693–734, New York, McGraw Hill.

Cox et al. (1977) "Actions of L–and D–Homocysteate in Rat CNS: A Correlation between Low–Affinity Uptake and the Time Courses of Excitation by Microelectrophoretically Applied L–Glutamate Analogues", *J. Neurochem* 29:579–588.

*Primary Examiner*—Jill Warden
*Assistant Examiner*—Jan M. Ludlow
*Attorney, Agent, or Firm*—Greenlee, Winner and Sullivan P.C.

[57] ABSTRACT

Method for quantifying the amounts of oxidized sulfhydryl amino acids, particularly cysteine sulfinic acid, cysteic acid, homocysteine sulfinic acid and homocysteic acid, for example, in biological samples are provided. The oxidized sulfhydryl amino acids are measured by gas chromatography/mass spectrometry after derivatization, preferably using stable isotope internal standards. Deviation from normal individuals' levels of oxidized sulfhydryl amino acids in serum are indicative of certain neuropsychiatric disorders, the biochemical origin of which can be diagnosed using methods disclosed herein, particularly when relative levels of these and/or other sulfur amino acids are measured.

7 Claims, 7 Drawing Sheets

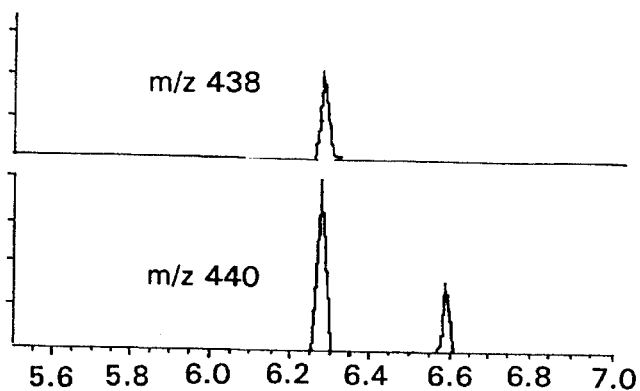
FIG. 2A
FIG. 2B
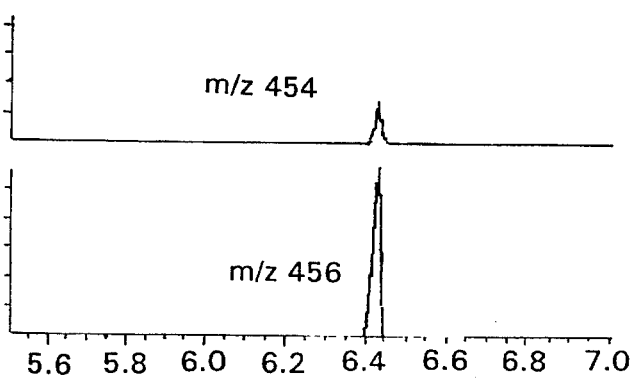
FIG. 2C
FIG. 2D
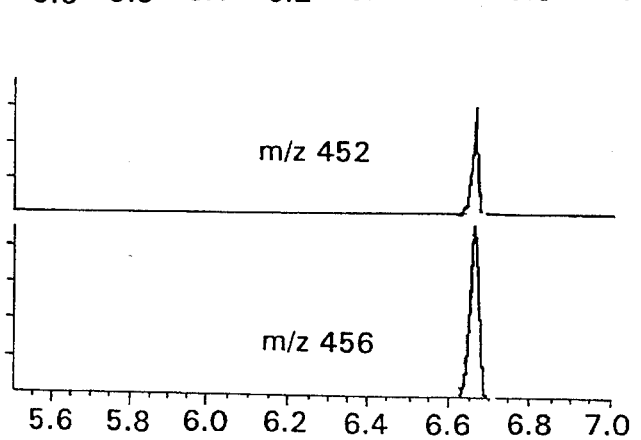
FIG. 2E
FIG. 2F
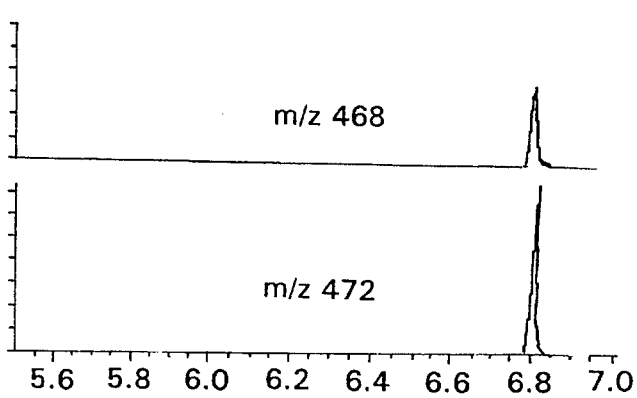
FIG. 2G
FIG. 2H
Time (min.)

Mass/Charge

Mass/Charge

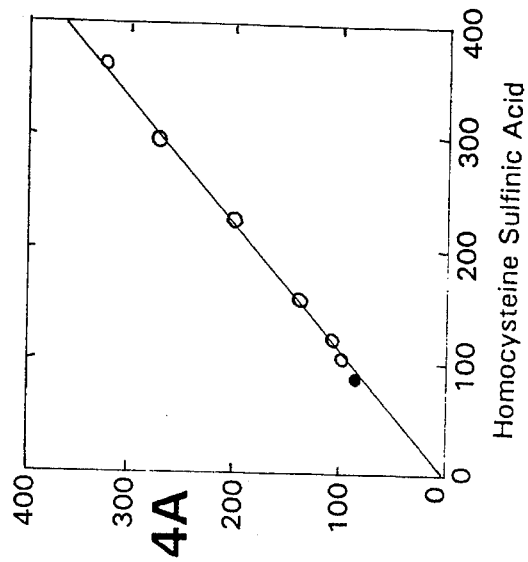
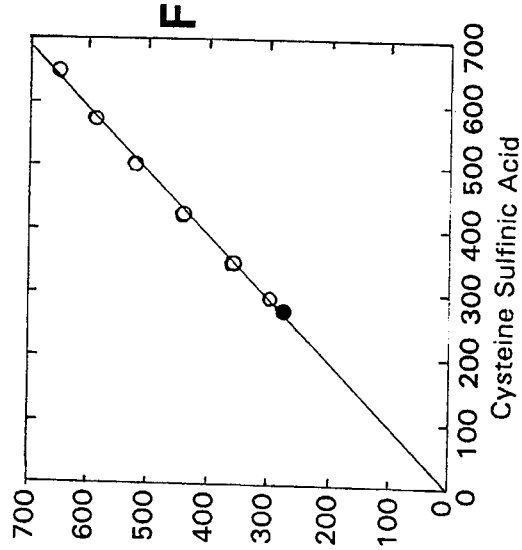
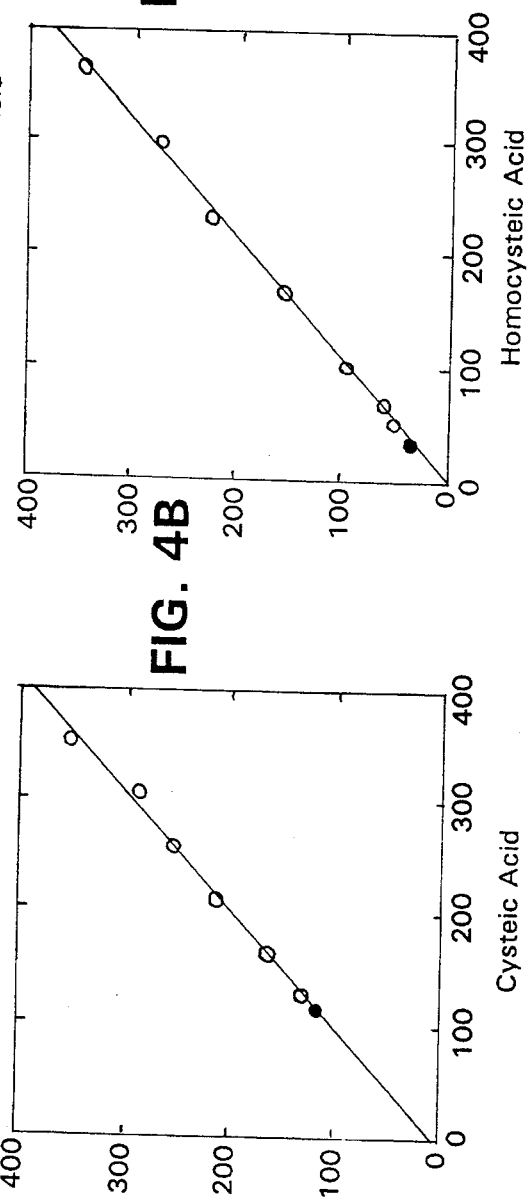

GAS CHROMATOGRAPHY/MASS SPECTROMETRY DETERMINATION OF OXIDIZED SULFHYDRYL AMINO ACIDS

This invention was made at least in part with funding from the National Institutes of Health (award 1-F 32-HDO7647) and from the Veterans Administration (RAGS award 0001). Accordingly the United States Government may have certain rights in this invention.

FIELD OF THE INVENTION

This invention pertains to methods for quantifying oxidized sulfur-containing amino acids in a sample, for example, by gas chromatography/mass spectrometry using stable isotope internal standards, in particular, measurement of homocysteine sulfinic acid, homocysteic acid, cysteine sulfinic acid and cysteic acid. The sample may be a biological fluid, such as serum, urine or cerebrospinal fluid.

BACKGROUND OF THE INVENTION

Several sulfur-containing amino acids (SAA) have been shown to be potent agonists of excitatory amino acid receptors in the mammalian central nervous system [Griffiths, R. (1993), *Biochem. Soc. Trans.* 21:66–72; Mewett et al. (1983), in Mandell, P., DeFeudis, F. V. (eds) *CNS Receptors: From Pharmacology to Behaviour*, 163–174, Raven Press, New York; Cox et al. (1977) *J. Neurochem* 29:579–588]. Homocysteine sulfinic acid ($HC-SO_2$) and homocysteic acid ($HC-SO_3$) are sulfur-containing homologues of glutamic acid, while cysteine sulfinic acid ($C-SO_2$) and cysteic acid ($C-SO_3$) are homologues of aspartic acid. These compounds are released on depolarization, bind to specific receptor sites in the brain and have been demonstrated immunocytochemically in various parts of the mammalian brain [Cox et al. (1977) supra; Luini et al. (1984) Brain Res. 324:271–277; Cuenod et al. (1990) *J. Histochem. Cytochem.* 38:1713–1715]. Homocysteic acid has been shown to be agonistic to pre- and post-synaptic N-methyl-D-Aspartate (NMDA) receptors [Do et al. (1986) *J. Neurochem.* 46:779–786; Smirnova et al. (1993) *Science* 262:430–433]. $HC-SO_2$ and $HC-SO_3$ are thought to be generated endogenously from the oxidation of homocysteine [Do et al. (1988) *J.Neural. Transm.* 72:185–190] while $C-SO_2$ and $C-SO_3$ are thought to arise endogenously from oxidation of cysteine. The structures of the sulfhydryl amino acids and the oxidized derivatives are shown in Scheme I herein.

Homocysteine itself arises predominantly from methionine through the transmethylation pathway involving S-adenosylmethionine (SAM), the universal physiologic methyl donor. Enzymatic reactions involving conversion of homocysteine to cystathionine, cystathionine to cysteine, cysteine to $C-SO_2$ and $C-SO_2$ to $C-SO_3$ have been described [Mudd et al. (1989) in Scriver, C. R. et al. (eds) *Disorders of Transsulfuration*, p.695, New York, McGraw Hill; Ohmori et al. (1972) *Physiol. Chem. & Physics.* 4:286–294]. As these SAA are generally derived from endogenous homocysteine, measurement of these compounds is of interest in clinical situations with potential homocysteinemia. Homocysteinemia is known to occur in deficiency of folate, cobalamin or pyridoxine or in inborn errors of metabolism such as cystathionine β-synthase deficiency or 5,10,methylenetetrahydrofolate reductase deficiency [Mudd et al. (1989) supra; Olszewski et al. (1993) *Free Radical Biol. Med.* 14:683–693; Stabler et al. (1988) *J. Clin. Invest.* 81:466–474]. Classic homocystinuria (secondary to cystathionine β-synthase deficiency) leads to a variety of organ system disturbances including neuropsychiatric illness [Mudd et al. (1989) supra]. Deficiency of folate, cobalamin and pyridoxine also causes neuropsychiatric disturbances [Stabler et al. (1988) supra; Shorvon et al. (1980) *Br. Med. J.* 281:1036–1038; Driskell, J. A. (1984) in Machlin L. J. (Ed.) *Handbook of Vitamins*, p. 379, New York, Marcel Dekker]. In a study of neurosurgical biopsy samples, the concentration of homocysteic acid in brain tissue in a subgroup of patients with intractable depression was elevated as compared to other patients [Francis et al. (1989) *Brain Res.* 494:315–324].

$HC-SO_2$ and $HC-SO_3$ have been isolated from the urine of patients with cystathionine β-synthase deficiency using paper chromatography [Ohmori et al. (1972) supra]. High performance liquid chromatography (HPLC) based methods utilizing a combination of external standards and retention times have been described for measurement of these compounds in brain tissue [Grieve and Griffiths (1992) *Neuroscience Letters* 145:1–5]. It has been suggested that a combination of internal standards and mass spectrometry is necessary for definitive identification and measurement of these SAA in tissues [Grieve and Griffiths (1992) supra; Klancnik et al. (1992) *Neuroscience* 49:557–570]. Measurement of these oxidation products of cysteine and homocysteine with certainty in human or animal serum is not believed to have been reported previously.

While various HPLC methods have been reported for determining levels of sulfur-containing amino acids in tissue samples, the identification of those compounds has not been absolute according to Grieve and Griffiths (1992) supra, who report that the identification was based on synchronization of retention times, "spiking" of samples with authentic markers, or a combination of those strategies. Grieve and Griffiths (1992) supra, further characterized Klancnik et al. (1992) supra, as reporting that the unequivocal identification of sulfur-containing amino acids is "currently unattainable due to a number of technical difficulties."

Thus, there is a need in the art for a sensitive and definitive assay for the measurement of homocysteine sulfinic acid, homocysteic acid, cysteine sulfinic acid and cysteic acid in biological and other samples, especially with application to the diagnosis of certain neuropsychiatric disorders of biochemical origin.

SUMMARY OF THE INVENTION

The subject method comprises a gas chromatography/mass spectrometry (GC/MS) method for the determination of one or more oxidized sulfhydryl amino acids in a biological sample. Said oxidized sulfhydryl amino acids include cysteine sulfinic acid, cysteic acid, homocysteine sulfinic acid and homocysteic acid. The methods disclosed herein are more sensitive than prior art methods and offer the additional advantage that cysteine sulfinic acid, cysteic acid, homocysteine sulfinic acid and homocysteic acid can be unambiguously identified when assayed together with stable isotope-labeled internal standards. Any loss of endogenous oxidized sulfur amino acids prior to quantitation can be determined by adding one or more internal standards prior to sample processing.

The subject method for determination of in vivo concentration in a body fluid of one or more oxidized sulfhydryl amino acids selected from the group consisting of cysteine sulfinic acid, cysteic acid, homocysteine sulfinic acid and homocysteic acid comprises the steps of combining a known amount of at least one internal standard with a biological sample collected in vitro, said biological sample comprising at least one of said oxidized sulfhydryl amino acids, at least partially purifying said endogenous and internal oxidized sulfhydryl amino acids from other components in said in vitro body fluid, quantitating said endogenous oxidized sulfhydryl amino acid concentrations in said purified in vitro body fluid by gas chromatography/mass spectrometry analysis, and determining the in vivo concentration of said oxidized sulfhydryl amino acid(s) by correcting the quantitated in vitro endogenous concentration for endogenous loss as reflected by the loss in said known amount of said internal standard.

Biological samples in which oxidized sulfhydryl amino acids can be measured include serum, as exemplified herein, as well as urine, cerebrospinal fluid, saliva, semen, pleural fluid, peritoneal fluid and amniotic fluid. These samples may be of human origin or they may be taken from animals other than humans. Additionally, extracts or microdialysates of tissue samples may be used as biological samples. Preferably the biological samples are of mammalian origin. As will be apparent to those skilled in the art, the subject method can also be used to quantitate oxidized sulfhydryl amino acids in fluids other than biological samples.

Preferably, the internal standard is a nonradioactive heavy isotope of the substance to be measured, which is advantageous in that through mass spectrometry, it provides more accurate measurement than radiolabeled substances and in that nonradioactive isotopes are safe for the environment. Preferably the internal standard is a stable isotope compound. Preferred internal standards for use in the instant GC/MS methods for cysteine sulfinic acid and cysteic acid are $[3,3-^2H_2]$-cysteine sulfinic acid and $[3,3-^2H_2]$-cysteic acid, respectively. Preferred internal standards for homocysteine sulfinic acid and homocysteic acid are $[3,3,4,4-^2H_4]$-homocysteine sulfinic acid and $[3,3,4,4-^2H_4]$-homocysteic acid, respectively. The structures of the subject sulfhydryl amino acids are given in Scheme I, and the asterisks (*) indicate replacement of $^2H$ for hydrogen in the stable isotope labeled compounds.

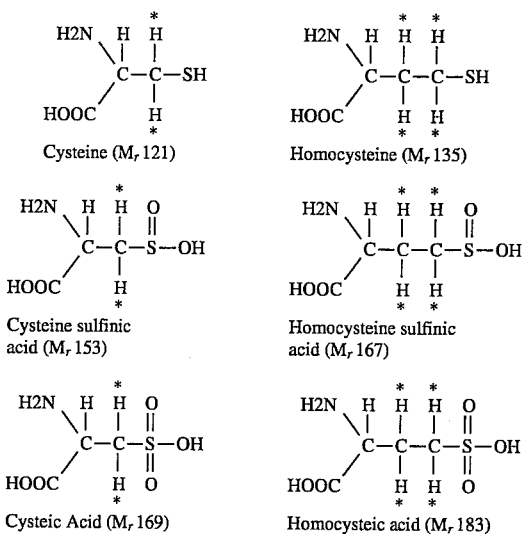

Scheme I

Deviations from normal human serum levels of the oxidized sulfhydryl amino acids are associated with certain psychiatric disorders, particularly those stemming from biochemical imbalance and/or metabolic deficiencies, including but not limited to schizophrenia and depression. Abnormality of OSAA could be an increase or decrease from normal range of a particular OSAA or be an alteration in the ratio of one to the other or alteration in the ratio of one OSAA to other neurotransmitters like GABA or Glutamate. The altered levels could be in brain tissue, cerebrospinal fluid or serum. Measurement of serum levels of one or more of cysteine sulfinic acid, cysteic acid, homocysteine sulfinic acid and homocysteic acid in patients suspected of psychiatric illness can be used in the diagnosis of psychiatric disorders, when the serum level of the one or more oxidized sulfhydryl amino acids is elevated as compared with normal individuals. Similarly, the measurement of oxidized sulfhydryl amino acid levels can allow the clinician to monitor a course of treatment, with a decrease in serum levels and/or a return to the normal range being indicative of successful treatment. Moreover certain biochemical imbalance and/or defects can be ascertained using the methods provided herein.

BRIEF DESCRIPTION OF THE DRAWINGS

FIGS. 2A–2H illustrate SIM chromatograms (m/z 150–650) of TBDMS-derivatized compounds as follows: FIG. 2A, cysteine sulfinic acid; FIG. 2B $[3,3-^2H_2]$cysteine sulfinic acid; FIG. 2C, cysteic acid; FIG. 2D $[3,3-^2H_2]$ cysteic acid; FIG. 2E, homocysteine sulfinic acid; FIG. 2F, $[3,3,4,4-^2H_4]$homocysteine sulfinic acid; FIG. 2G, homocysteic acid; FIG. 2H, $[3,3,4,4-^2H_4]$homocysteic acid.

in FIG. 3B for $[3,3-^{2H}_2]$cysteine sulfinic acid; in FIG. 3C for cysteic acid; in FIG. 3D for $[3,3-^2H_2]$cysteic acid; in FIG. 3E for homocysteine sulfinic acid; in FIG. 3F for $[3,3,4,4-^2H_4]$homocysteine sulfinic acid; in FIG. 3G for homocysteic acid; and in FIG. 3H for $[3,3,4,4-^2H_4]$homocysteic acid.

FIG. 4A–4D illustrate calibration curves of TBDMS derivatized oxidized sulfur amino acids in serum for the ion abundance of varying quantities of test compounds to stable isotope standards as follows: FIG. 4A for cysteine sulfinic acid; FIG. 4B for cysteic acid; FIG. 4C for homocysteine sulfinic acid; and FIG. 4D for homocysteic acid.

DETAILED DESCRIPTION OF THE INVENTION

Figure 1:
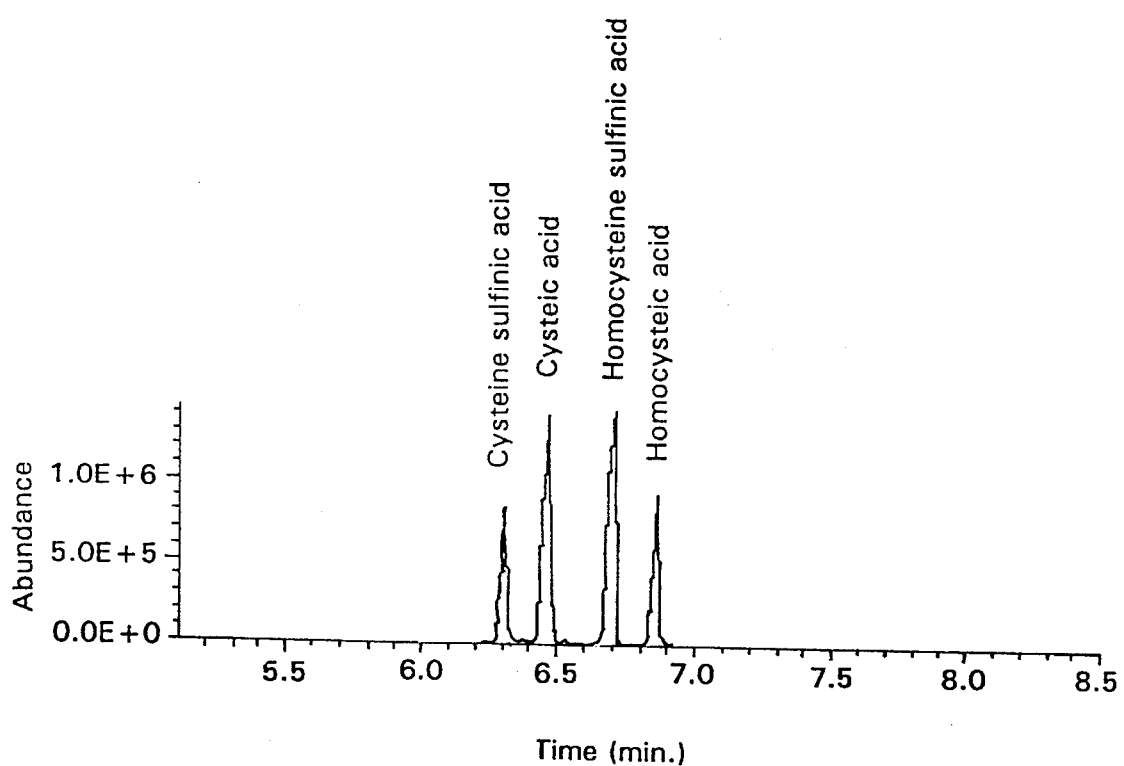
FIGS. 1 illustrates total ion chromatograms (TIC) of a mixture of MTBSTFA derivatized SAA and their corresponding stable isotope labelled internal standards.
Figure 3A:
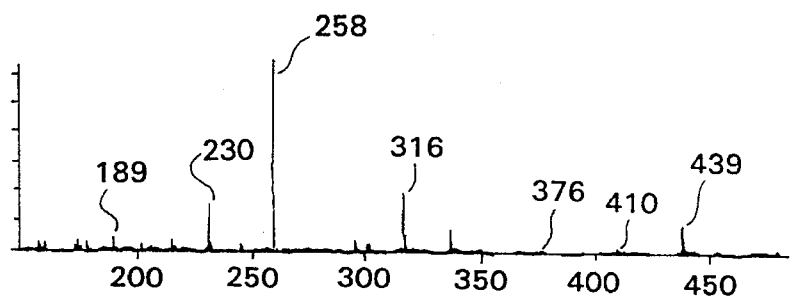
FIGS. 3A–3H illustrate the spectra of TBDMS-derivatized oxidized SAA compounds. $[M-57]^+$ m/z of each of the derivatives is indicated by an arrow in FIG. 3A for cysteine sulfinic acid.
Figure 3B:
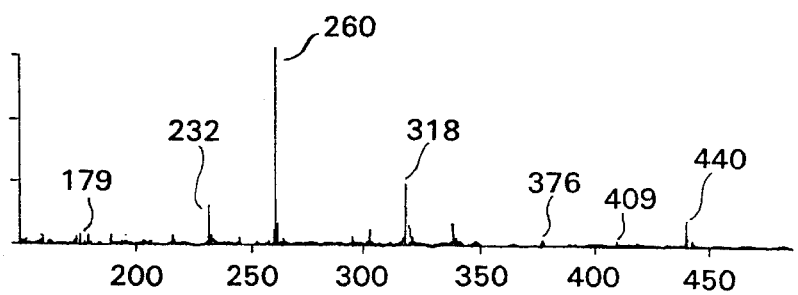
Figure 3C:
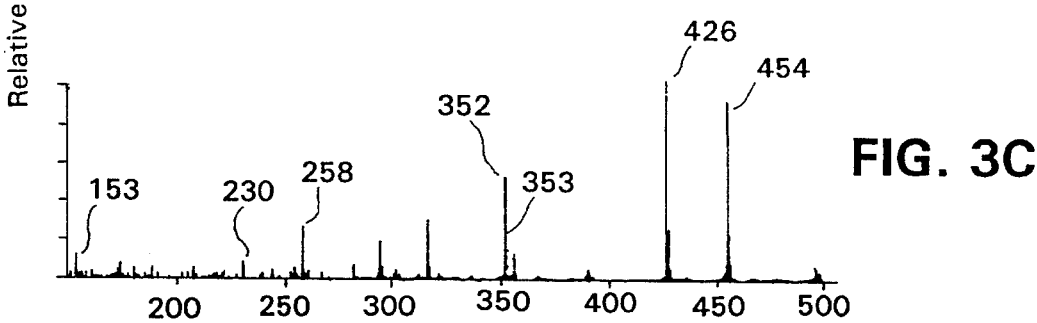
Figure 3D:
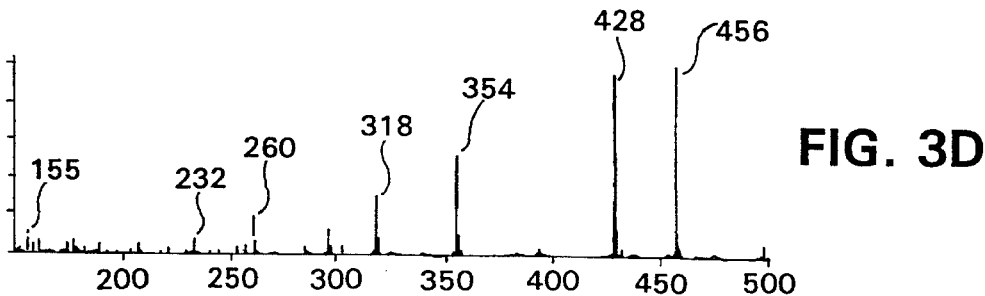
Figure 3E:
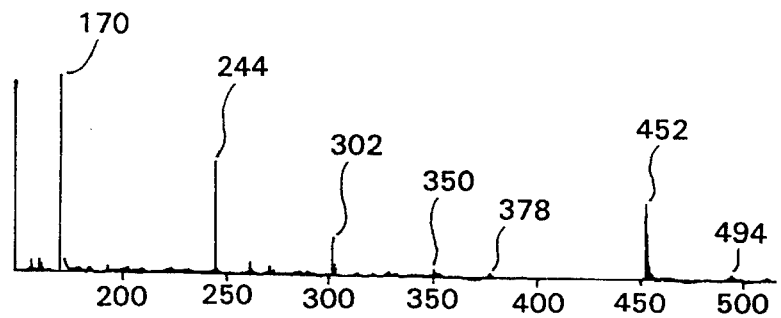
Figure 3F:
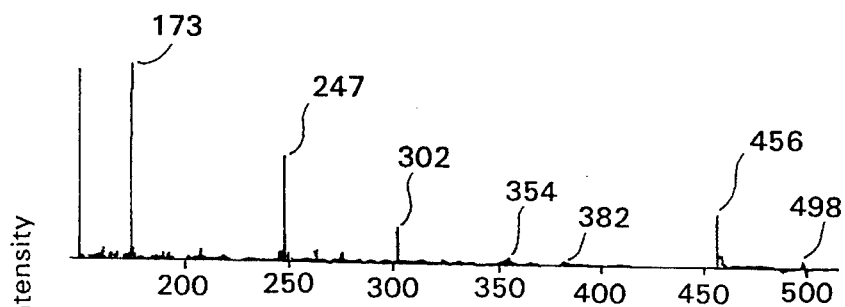
Figure 3G:
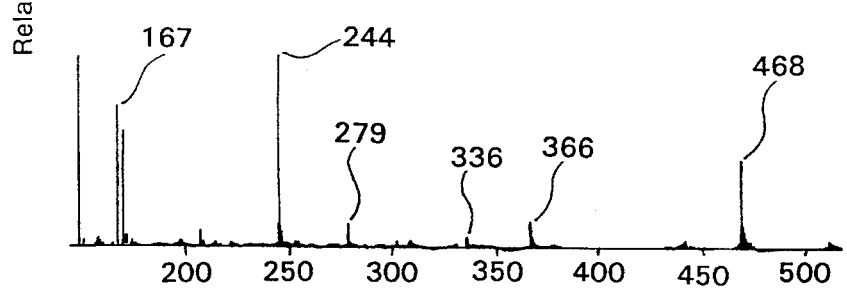
Figure 3H:
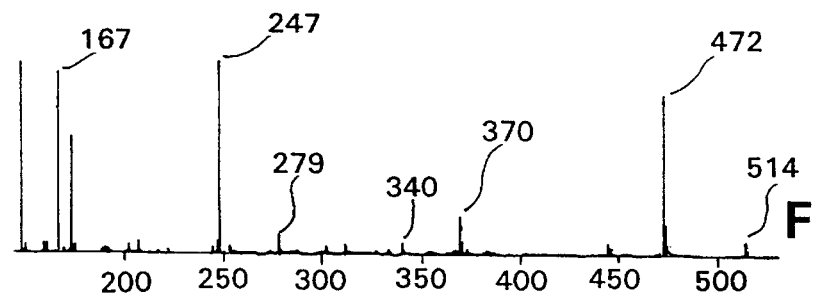

The subject invention provides a method of accurately and sensitively determining the in vivo concentrations of one or more oxidized sulfhydryl amino acids with correction for loss of endogenous oxidized sulfhydryl amino acids during sample storage and/or preparation. The GC/MS method taught herein is more sensitive than known methods for measurement of cysteine sulfinic acid, cysteic acid, homocysteine sulfinic acid and homocysteic acid and offers the advantage of unambiguous identification of these compounds. The use of internal standards also enables the determination of any potential loss of the endogenous oxidized sulfhydryl amino acids during sample processing.

The sulfhydryl amino acids are those containing an —SH moiety, e.g., homocysteine of the formula HOOC—CH(NH$_2$)—CH$_2$—CH$_2$—SH and cysteine of the formula HOOC—CH(NH$_2$—CH$_2$—SH. Oxidation of the sulfhydryl amino acids yields homocysteine sulfinic acid and homocysteic acid from homocysteine and cysteine sulfinic acid and cysteic acid from cysteine. As used herein the term "oxidized sulfhydryl amino acids" (OSAAs) encompasses homocysteine sulfinic acid, homocysteic acid, cysteine sulfinic acid and cysteic acid.

The internal reference standard is any suitable compound which will behave identically with the endogenous target compound throughout the procedure up to analysis on the mass spectrometer, but which is distinguishable under mass spectrometric analysis and can be separately measured. Examples of suitable internal standards are deuterated or tritiated analogs of the target oxidized sulfhydryl amino acids to be measured or deuterated or tritiated compounds sufficiently similar to the target compounds to be effectively identical to the target compound for the purposes of this assay, or other analogs of the target oxidized sulfhydryl amino acid containing sufficient amounts of $C^{13}$ or $N^{15}$ or other stable isotope markers. Thus, the labeled reference compound is indistinguishable from the unlabeled target compound during handling but will provide different and distinct ions for quantification on the mass spectrometer. Examples of preferred compounds for this assay are deuterated forms of cysteine sulfinic acid and cysteic acid, e.g., [3,3-$^2$H$_2$] cysteine sulfinic acid and [3,3-$^2$H$_2$]cysteic acid, respectively, and deuterated forms of homocysteine sulfinic acid and homocysteic acid, e.g., [3,3,4,4-$^2$H$_4$]homocysteine sulfinic acid and [3,3,4,4- $^2$H$_2$] homocysteic acid ( see also Scheme I herein ) . Compounds suitable for use as internal standards can be prepared from commercially available starting materials as described in Example 1 herein, or by any means known to the art.

Quantification is based on the assumption that the ratio of measured target compound to measured internal standard is the same as the ratio of total unknown target compound in the initial sample was to the total amount of added internal standard. This assumes that same recovery rate for both the target compound(s) and the internal standard(s). In quantitation, correction for natural isotopic abundance of stable isotopes is employed, as described in Example 4. No special handling is required for the standards, except that newly synthesized internal standards are kept as dry powder protected from light at −20° C.

Optionally, it may be necessary or desirable to purify the target compounds and internal standards before analysis. Any means known to the art for the purification and separation of amino acids, e.g., filtration, column chromatography, anion and/or cation exchange chromatography, gas chromatography, liquid chromatography, high pressure liquid chromatography, molecular sieving, etc., may be used. Methods of selecting suitable separation and purification techniques, and means of carrying them out, are known in the art. See, e.g., Labadarios et al. (1984) *J. Chrom.* 310:223–231 and references cited therein; Shahrokhi and Gehrke (1968) *J. Chrom.* 36:31–41. It is preferred that the oxidized sulfhydryl amino acids be at least partially purified before derivatization, for example, by ion exchange chromatography.

Optionally, it may be necessary or desirable to modify the target compound and the internal standard to alter or improve certain characteristics to facilitate purification and/or separation. This practice is well-known in the art as derivatization. For example, it may be desired to convert the target and reference compounds to analogs having improved solubility, different mass to charge ratio, increased volatility, etc., to facilitate purification and/or separation and identification for analysis on the gas chromatography/mass spectrometer. See., e.g., D. R. Knapp (1979) *Handbook of Analytical Derivatization Reactions*, John Wiley & Sons, New York. A preferred procedure involves converting the target and reference compounds to their silyl derivatives to facilitate separation and identification on a combined gas chromatograph/mass spectrometric apparatus. Means and methods of silylating compounds for this purpose are known in the art, see, e.g., Knapp, supra; Bierman et al. (1986) *J. Chrom.* 357:330–334. A preferred method involves combining the target compound(s) with internal reference standard(s), partially purifying the oxidized sulfhydryl amino acids in the combination, and incubating the product in a mixture of acetonitrile and N-methyl-N-t-butyldimethylsilyl trifluoroacetamide to achieve silation. The resulting silated target and reference oxidized sulfhydryl amino acids are then analyzed using the GC/mass spectrometer.

Combined GC/MS analysis has the advantage that cysteine sulfinic acid, cysteic acid, homocysteine sulfinic acid and homocysteic acid and their respective internal standards have distinct GC column retention times and/or distinct mass spectrometer fractionation patterns. Additionally, the GC/MS combined analysis method can be automated to further reduce processing time and labor and materials costs.

Based on the structure of each of the oxidized sulfhydryl amino acids and the possible derivatization sites, the masses of the SAAs and of the potential MTBSTFA derivatives and the [M-57]$^+$ ions were calculated according to standard methods. These values are displayed in Table I.

TABLE 1

Molecular Weights (M$_r$), Total Mass of TBDMS-Derivatized Products in Daltons (M$^+$) and [M-57]$^+$ m/z of Each of the Compounds Measured

| Compound | (M$_r$) | M$^+$ | [M-57]$^+$ m/z |
|---|---|---|---|
| Cysteine Sulfinic Acid | 153 | 495 | 438 |
| [3,3-$^2$H$_2$]Cysteine Sulfinic Acid | 155 | 497 | 440 |
| Cysteic Acid | 169 | 511 | 454 |
| [3,3-$^2$H$_2$]Cysteic Acid | 171 | 513 | 456 |
| Homocysteine Sulfinic Acid | 167 | 509 | 452 |
| [3,3,4,4-$^2$H$_4$]Homocysteine Sulfinic Acid | 171 | 513 | 456 |
| Homocysteic Acid | 183 | 525 | 468 |
| [3,3,4,4-$^2$H$_4$]Homocysteic Acid | 187 | 529 | 472 |

The total ion chromatograms of pure derivatized compounds are shown in FIGS. 1A–1H. C-SO$_2$ and [3,3-$^2$H$_2$] C-SO$_2$ eluted at 4.93 minutes, C-SO$_3$ and [3,3-$^2$H$_2$]C-SO$_3$ at 5.03 minutes, HC-SO$_2$ and [3,3,4,4-$^2$H$_4$]HC-SO$_2$ at 5.24 minutes and HC-SO$_3$ at 5.48 minutes and [ 3,3,4,4-$^2$H$_4$]HC-SO$_3$ at 5.50 minutes All compounds yielded single major peaks.

Mass spectra of each of the derivatized OSAAs with their corresponding stable isotope standards are shown in FIGS. 2A–2H. The total mass of derivatized products (M$^+$) and the [M-57]$^+$ ion of each compound is shown in Table 1. The ratio of [M-57]$^+$ ion of native compound to known quantity of stable isotope labelled internal standard was used for quantitation.

Calibration curves of each oxidized sulfhydryl amino acid in serum are shown in FIGS. 3A–3H. Calibration curves were derived by plotting the ratio of the abundances of test compounds to fixed amounts of stable isotope labeled compounds against increasing quantities of test compounds. For example, varying amounts of C-SO$_2$ were added to 100 μL normal serum aliquots before purification. Each sample was purified and analyzed as described herein. The amount of C-SO$_2$ measured was calculated by multiplying the amount of added [3,3-$^2$H$_2$]C-SO$_2$ with the ratio of abundances at m/z 438 to 440. This gives the amount of C-SO$_2$ in 100 μL serum. The measured C-SO$_2$ level is plotted against the predicted level of C-SO$_2$. The predicted level is the sum of the amount added and the measured value in the normal serum to which no exogenous OSAA was added. The ratio of ions was linear at the tested range with a correlation coefficient (r) of 0,994 for C-SO$_2$, 0.994 for C-SO$_3$, 0.998 for HC-SO$_2$ and 0.999 for HC-SO$_3$.

In normal serum, OSAAs are present in nanogram quantities. The amount of serum used for sample preparation was 100 μL and the electron multiplier (EM) setting used for measurement was 1800 V. It is possible to increase sensitivity of measurement several fold by adjusting sample size and EM setting, as is readily apparent to one of ordinary skill in the art. The use of stable isotope internal standards and mass spectrometry provides for specificity of the measurement and correction for losses during sample preparation. The stable isotopes used in this method are prepared in the laboratory from commercially available stable isotopically labeled compounds. The method of measurement of these compounds could be easily adapted for use in other biological samples.

To test whether oxidized SAAs were generated ex vivo during sample preparation, experiments were conducted by adding varying amounts of homocystine (10 to 100 times physiological levels) to 100 μL serum samples at the beginning of the sample preparation process. Analysis of these samples did not show any measurable conversion of homocystine to HC-SO$_2$ or HC-SO$_3$.

To determine the lower limits for detection of OSAAs in aqueous solution, decreasing quantities of OSAAs were added to fixed amounts of stable isotope internal standards and assayed with an EM setting of 3000 V in the SIM mode for the mass spectrometry step. The limit of detection of SAA ranged from 5–80 fmols (5 fmols for C-SO$_2$ and HC-SO$_2$, 20 fmols for C-SO$_3$ and 80 fmols for HC-SO$_3$). The assay is linear over a tested range of 0.1 nmol to 100 nmol each of the compounds.

Values for each oxidized SAA were then determined on fasting serum samples from 20 apparently normal individuals (11 males, 9 females, age range 19–55 years). The mean values and standard deviations were 210±43 ng/ml (1373±281 pmols/ml) for C-SO$_2$, 117±18 ng/ml (692±107 pmols/ml) for C-SO$_3$, 113±35 ng/ml (677±210 pmols/ml) for HC-SO$_2$ and 34±7 ng/ml (186±38 pmols) for HC-SO$_3$. A normal range was determined for each SAA using the mean value ±2 standard deviations (FIG. 4).

The potential clinical implications of the presence of these compounds in serum are not known at the present time, but altered levels (as compared with ranges for normal individuals) of the oxidized SAA are correlated with neuropsychiatric illness, as taught herein. C-SO$_3$, HC-SO$_3$, HC-SO$_2$ and C-SO$_2$ have been reported to cause excitatory effects on neurons of the central nervous system through activation of N-methyl-D-aspartic acid receptors in striatum, cortex, hippocampus, retina, dorsolateral geniculate nucleus and spinal cord of animals [Do et al. (1986) Supra; Do et al. (1988) supra; Francis et al. (1989) supra; Grieve and Griffiths (1992) supra].

Studies using [$^{35}$S]-methionine in rat brain slices indicate that a source of endogenous HC-SO$_2$ is methionine which has been cycled through the transmethylation pathway involving S-adenolsylmethionine and S-adenosylhomocysteine [Do et al (1988) supra].

Since the source of most of the oxidized SAAs is from endogenous homocysteine, it is predicted that these oxidation products are elevated in serum in conditions of hyperhomocysteinemia. Folate deficiency, which causes megaloblastic anemia and depressive symptoms, is a common cause of hyperhomocysteinemia, and serum homocysteine levels are known to correct to normal ranges within days of folate treatment [Stabler et al. (1988) supra; Shorvon et al. (1980) supra]. In a study of experimental human folate deficiency, the subject's depressive mood changed to one of euphoria within days of folate repletion (Herbert, V. (1962) Trans. Assoc. Am. Phys. 75: 307–320). Without wishing to be bound by any particular theory, it is postulated that those mood swings were related to changes in oxidized SAA secondary to changes in homocysteine levels.

Dysfunction of NMDA receptor-mediated glutaminergic transmission has been proposed to play a role in the etiology and pathogenesis of schizophrenia (Deutch et al. (1989) Clin. Neuropharmacol 12: 1–13; Olney, J. W. (1989) Biol. Psychiatry 26: 505–525). Oral methionine loading, which causes transient hyperhomocysteinemia, is known to exacerbate psychotic symptoms in chronic schizophrenia (Cohen et al. (1974) Biol. Psychiatry 8: 209–225) and several studies (Vahora et al. (1988) Neurosci. & Behavioural Rev. 12: 139–141) have shown S-adenosyl-methionime to be an effective treatment for depression. It is possible that these mood changes are mediated through excitatory sulfur amino acids acting on NMDA receptors.

NMDA receptors are involved in physiologic mechanisms, including long-term potentiation and excitotoxicity, and excessive activation of NMDA receptors is implicated in the pathogenesis of several other neurological conditions ranging from toxic and metabolic encephalopathies to neurodegenerative disorders (Shaw, P. J. (1993) Curr. Opin. Neurol. Neurosurg. 6: 414–422). Measurement of the endogenous oxidized SAA agonists of these receptors can be useful in diagnosis and/or prognosis of these conditions. For example, treatment of a particular neuropsychiatric condition in which OSAAs are altered, could be monitored by periodically measuring serum and/or cerebrospinal fluid levels of OSAAs.

NMDA (n-methyl-d-aspartate) receptors are a subtype of glutamate receptors in the mammalian central nervous system. They are voltage- and ligand-gated channels for influx of sodium and calcium. Glutamate is thought to be the usual transmitter in the NMDA synapses. Increased transmission in these receptors leads to a phenomenon called excitotoxicity, whereby increased calcium influx causes activation of cellular proteases and eventual neuronal degeneration and death. It may be the ultimate pathway of apoptosis in neurons. NMDA receptor mediated excitotoxicity has been implicated as a final common pathway for several neurological disorders, including Huntington's disease, AIDS dementia complex, neuropathic pain syndromes, and perhaps nonketotic hyperglycemia, hydroxybutyric aminoacidemia, and treatment for drug addiction, tolerance and dependency.

Figure 5:
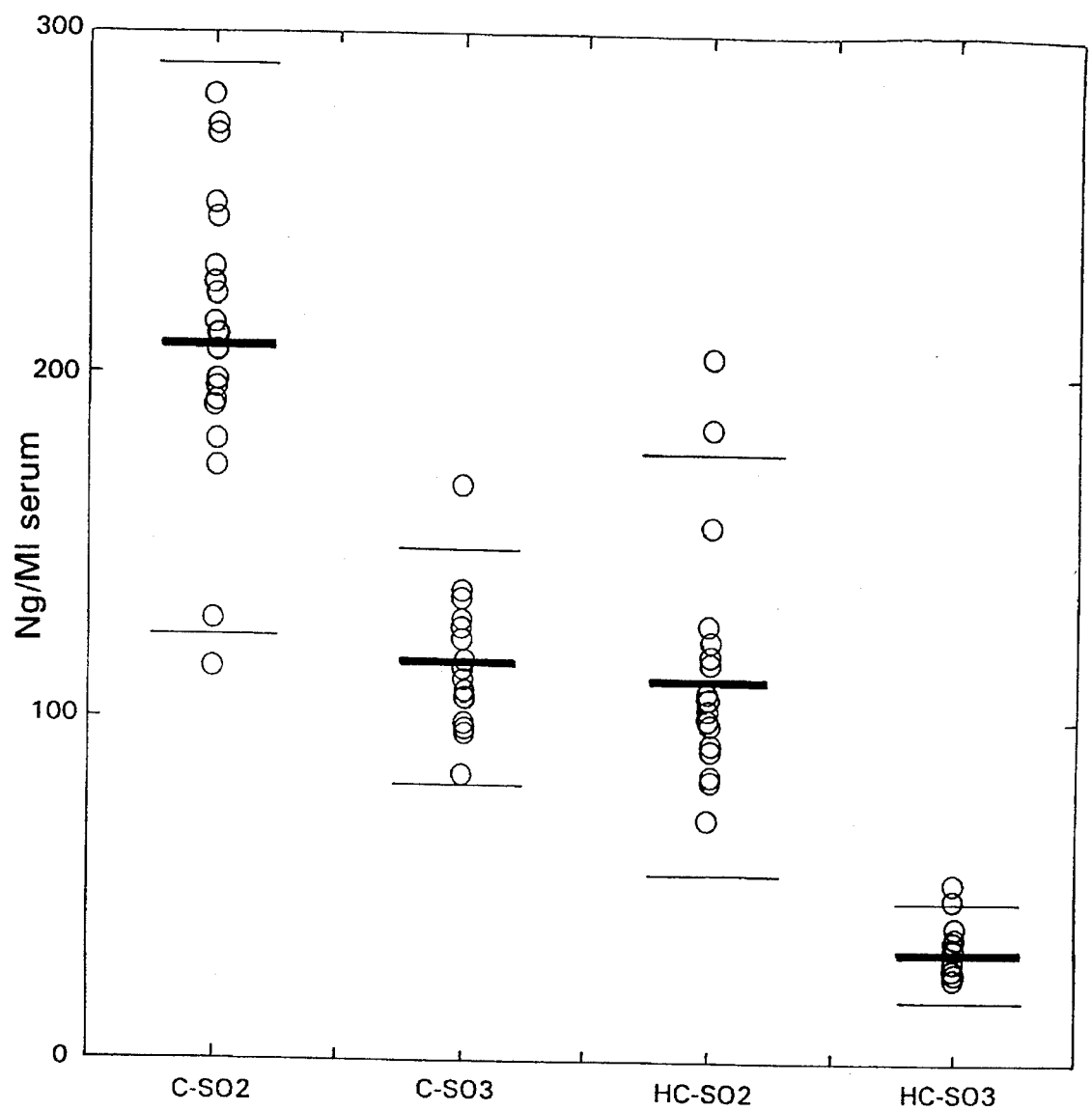
FIG. 5 illustrates the normal range determinations for oxidized sulfur amino acids in human serum (n=20). $C-SO_2$ is cysteine sulfinic acid, $C-SO_3$ is cysteic acid, $HC-SO_2$ is homocysteine sulfinic acid and $HC-SO_3$ is homocysteic acid. The heavy bars indicate means; each thin bar indicates mean ±2 SD.
Figure 6:
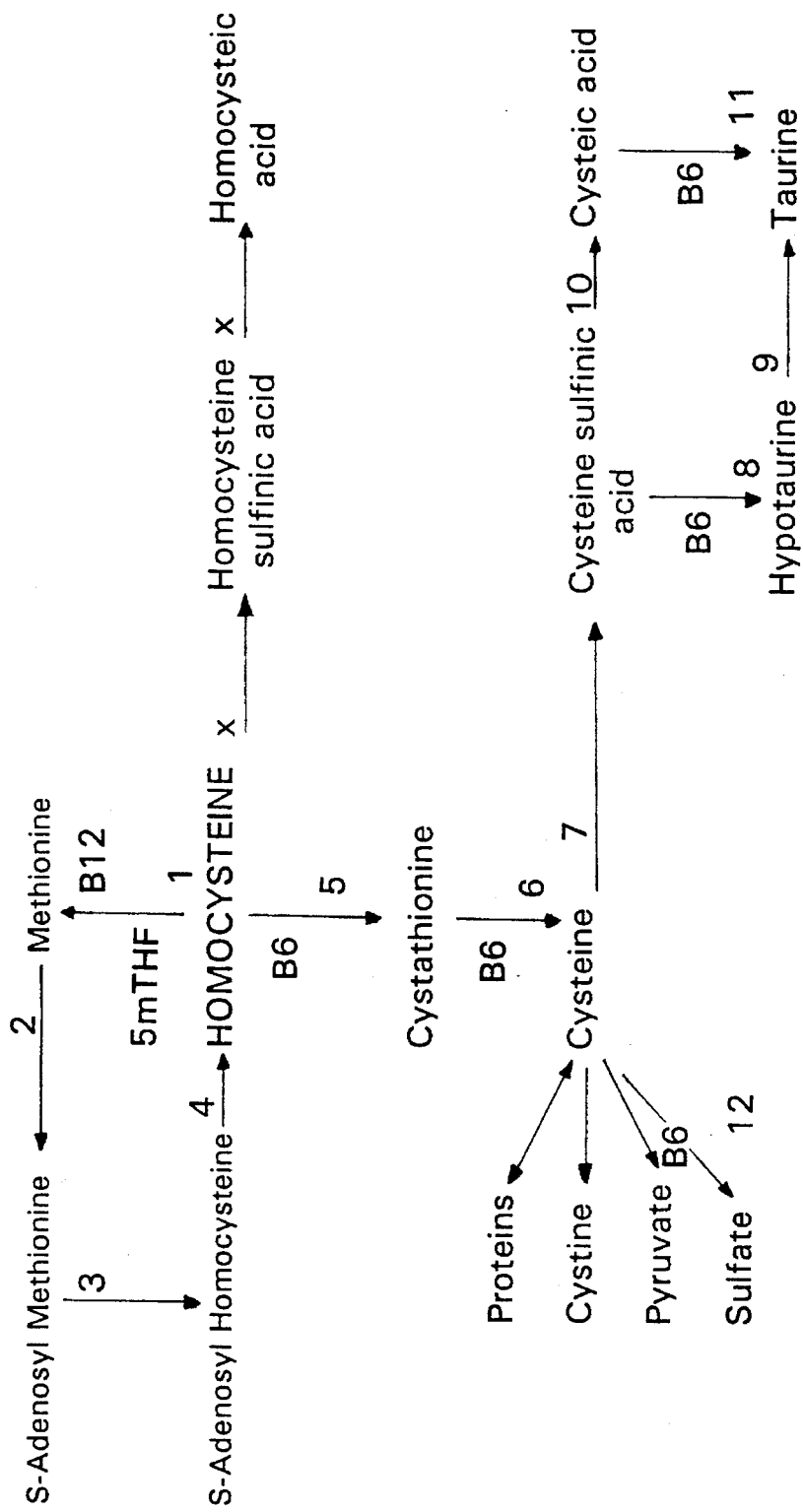
FIG. 6 illustrates metabolic pathways of homocysteine catabolism in mammalian brain.

FIG. 5 summarizes metabolic pathways for the catabolism of homocysteine in mammalian brain. Disruption of one or more of the reactions displayed can lead to biochemical imbalance, which can lead to neurological and/or psychiatric disorders. Misra and Olney (1975) *Brain Res.* 97:117–126 refer to errors of sulfur amino acid metabolism as "relatively common metabolic disorders" and state that "serious neuropsychiatric disturbances frequently accompany such disorders."

Cysteine sulfinic acid, cysteic acid, homocysteine sulfinic acid and homocysteic acid are potent agonists of NMDA receptors. Indeed cysteine sulfinic acid and homocysteic acid have been considered endogenous agonists of NMDA receptors. As these compounds can induce excitotoxicity, it is postulated that an accumulation of these substances could result in neurological damage. Alterations in brain levels (as compared with levels in normal individuals) of these compounds are measurable in body fluids, including but not limited to cerebrospinal fluid.

A deficiency of sulfite oxidase results in defective degradation of cysteine to sulfate and can lead to accumulation of cysteine and its oxidation products ($C-SO_2$ and $C-SO_3$). Sulfate oxidase deficiency is associated with a neurological disorder in early childhood.

Cysteine dioxygenase catalyzes the conversion of cysteine to cysteine sulfinic acid (Reaction 7 in FIG. 5). A deficiency of this enzyme is predicted to lead to elevated cysteine levels and low $C-SO_2$ and $C-SO_3$ levels. This enzyme is known to be grossly deficient in Hallervorden-Spatz disease, which is characterized by the onset of Parkinsonism in early childhood (Perry et al. (1985) *Ann. Neurol.* 18:482–489). Heterozygosity for the deficient enzyme may be the genetic explanation for similar neurodegenerative disorders. Clinically, Hallervorden-Spatz disease is characterized by progressive dementia, bradykinesia, rigidity, spasticity, dystonia and choreoathetosis. The deficiency may be evident only in certain tissues and/or biological fluids, e.g., brain tissue and/or cerebrospinal fluid. Other neurological disorders considered to be associated with defects in this enzyme include Alzheimer's disease, Parkinsonism, Motor Neuron Disease and Huntington's disease. Work by Perry et al. (Neurology 1991) and Heafield (NeuroSci. Lett. 1990) showed conflicting results on measurement of cysteine sulfinic acid or cysteine using HPLC or amino acid analyzer, both of which are suspect methods. There are no reports of measurement of OSAAs in serum or CSF as the technology has not been reported. An abnormality of conversion of cysteine sulfinic acid to cysteic acid (enzymatic or free radical mediated, Reaction 10 in FIG. 5) results in high levels of cysteine sulfinic acid and cysteine, and the lack of or abnormally low levels of $C-SO_3$. Both cysteine and cysteine sulfinic acid are excitotoxins and consequently, may be involved in neurogenerative disorders.

Deficiencies in the conversion of cysteine sulfinic acid to hypotaurine and/or cysteic acid to taurine are believed to cause levels of cysteine sulfinic acid and cysteic acid to rise. Alternatively, levels of taurine may rise and hypotaurine fall in an abnormality of conversion of cysteine sulfinic acid to hypotaurine. High levels of taurine and low levels of cysteine have been demonstrated in the serum of patients with the acquired immunodeficiency syndrome (AIDS). Thus, without wishing to be bound by any particular theory, an alteration of the profile of sulfur amino acids may result in AIDS-encephalopathy and other diseases with neuropsychiatric manifestations. Enzyme systems have not been described for the conversion of homocysteine to homocysteine sulfinic acid (Reaction X, FIG. 5) and homocysteine sulfinic acid to homocysteic acid (Reaction x, FIG. 5), probably due to the fact that the substrates and products could not be measured in any specific fashion in the past. In hereditary homocystinuria due to cystathionine-β-synthase deficiency, excess homocysteine sulfinic acid and homocysteic acid are excreted in the urine, and elevated levels, relative to those of normal individuals, are detectable in serum samples.

Francis et al. (1989) supra reports elevated homocysteic acid and aspartic acid levels in the brains of patients with simple intractable depression as compared to control individuals and psychotic depression patients. Francis et al. (1989) supra also refers to authentic $HC-SO_3$ as not being amenable to analysis either by GLC or HPLC with mass spectrometry.

U.S. Pat. No. 4,940,658 (Allen et al., issued Jul. 10, 1990) refers to diagnoses of cobalamin and folic acid deficiencies. Both cobalamin (as Vitamin $B_2$) and folate (as 5-Methyl tetrahydrofolate) are co-factors in Reaction 1 in FIG. 5. A deficiency of either cofactor leads to hematological abnormalities, and while administration of either cofactor will ameliorate the blood disturbance, only the appropriate cofactor will correct the neuropsychiatric abnormalities. In warm blooded animals folate deficiency causes elevated homocysteine levels and cobalamin deficiency is diagnosed when homocysteine and methylmalonic acid levels are elevated. Symptoms of both deficiencies result in serious and potentially life threatening neuropsychiatric abnormalities.

In order to confirm the association between neuropsychiatric disorders and deviations from the normal serum levels of one or more of the oxidized sulfhydryl amino acids, blood samples from twenty normal individuals and from twenty randomly chosen psychiatric inpatients were analyzed for folates, cysteine (C-SH), homocysteine (HC-SH) and the OSAAs. Folates were measured because folate deficiency can be manifested by psychiatric disorders so that any deviation in OSAAs secondary to folate deficiency could be noted.

Of the twenty psychiatric inpatients, only one patient was found to have low serum folate (<3ng/ml) and three were found to have low RBC folates (<180ng/ml, performed using competitive binding assays). All three (patients 2, 3, and 9 of Table 2) belonged to the group of affective disorders. Folate coenzyme profiles are not reported herein. The results of analysis of cysteine, homocysteine and their oxidation products of fifteen patients (see Table 2) indicate significant differences between groups. The remaining five patients, who lacked a discrete psychiatric diagnosis and were admitted for substance abuse, other medical problems or dementia, had normal values and are not shown in this analysis.

TABLE 2

| Patient ID # | Diagnosis | C-SH µmols/L | C-SO2 nmols/L | C-SO3 nmols/L | HC-SH µmols/L | HC-SO2 nmols/L | HC-SO3 nmols/L | HCSO2/ HCSO3 | CSO2/ CSO3 |
|---|---|---|---|---|---|---|---|---|---|
| 1 | Bipolar Manic with psychotic | 282 | 1990 | 95 | 8.08 | 133 | 4.94 | 26.90 | 20.89 |
| 2 | Bipolar Manic with psychotic | 124 | 2076 | 391 | 12.64 | 125 | 14.36 | 8.71 | 5.32 |

TABLE 2-continued

| Patient ID # | Diagnosis | C-SH μmols/L | C-SO2 nmols/L | C-SO3 nmols/L | HC-SH μmols/L | HC-SO2 nmols/L | HC-SO3 nmols/L | HCSO2/ HCSO3 | CSO2/ CSO3 |
|---|---|---|---|---|---|---|---|---|---|
| 3 | Bipolar, Manic | 300 | 2145 | 254 | 14.14 | 80 | 6.83 | 11.71 | 8.44 |
| 4 | Bipolar Mood Disorder | 218 | 1487 | 184 | 4.68 | 82 | 8.63 | 9.49 | 8.08 |
| 5 | Bipolar Mood Disorder | 296 | 1726 | 254 | 7.50 | 121 | 7.26 | 16.71 | 6.81 |
| 6 | Dysthymia | 228 | 1880 | 251 | 5.44 | 65 | 8.20 | 7.86 | 7.50 |
| 7 | Major Depression | 292 | 1636 | 149 | 10.19 | 63 | 6.47 | 9.81 | 10.99 |
| 8 | Depressive Disorder | 297 | 2130 | 317 | 8.25 | 113 | 5.57 | 20.23 | 6.71 |
| 9 | Major Depression, acohol abuse | 228 | 1736 | 223 | 20.23 | 457 | 8.87 | 51.50 | 7.77 |
|  | MEAN | 252 | 1867 | 235 | 10.13 | 138 | 7.90 | 18.10 | 9.17 |
|  | SD | 59 | 235 | 88 | 4.88 | 123 | 2.76 | 14.04 | 4.66 |
| 10 | Chr Para Schiz | 277 | 1846 | 230 | 8.88 | 60 | 4.47 | 13.41 | 8.04 |
| 11 | Chr Para Schiz | 320 | 1856 | 255 | 15.34 | 89 | 7.09 | 12.54 | 7.29 |
| 12 | Chr Dis Schizo | 356 | 2213 | 327 | 13.11 | 99 | 6.14 | 16.17 | 6.77 |
| 13 | Chr Undiff Schizo | 282 | 2074 | 226 | 11.50 | 148 | 6.92 | 21.46 | 9.19 |
| 14 | Chr Para Schiz, Depressed | 233 | 1642 | 149 | 5.15 | 88 | 5.93 | 14.92 | 11.00 |
| 15 | Chr Para Schiz, alchol abuse | 341 | 1742 | 257 | 6.01 | 75 | 6.18 | 12.08 | 6.77 |
|  | MEAN | 301 | 1895 | 241 | 10 | 93 | 6.12 | 15.10 | 8.18 |
|  | SD | 46 | 212 | 58 | 4 | 30 | 0.93 | 3.47 | 1.66 |
|  | Mean of normal (N = 20) | 285 | 1456 | 285 | 7.58 | 77 | 27.93 | 6.32 | 5.98 |
|  | SD of normal controls | 25 | 359 | 91 | 2.59 | 48 | 22.58 | 5.94 | 2.99 |

Statistical analysis revealed that mean homocysteine, homocysteine sulfinic acid and cysteine sulfinic acid levels were higher in the affective disorder group compared to normal controls (p=0.13 for homocysteine, p=0.12 for homocysteine sulfinic acid and p=0.006 for cysteine sulfinic acid on unpaired t test). Homocysteic acid levels were lower for the patient group as a whole than for the normal group. The ratio of homocysteine sulfinic acid to homocysteic acid was higher in the affective disorder group compared to normal controls (p=0.014) and between schizophrenia group and control group (p=0.03). These differences are probably real as the cysteine sulfinic acid to cysteic acid ratio is not different between groups. It is proposed that the deviation in the HC-SO$_2$ to HC-SO$_3$ ratio in the psychiatric patients contributes to their psychiatric symptoms.

In B$_6$ (pyridoxine) deficiency reactions 5 and 6 and other reactions downstream in cysteine degradation are blocked, and the levels of HC-SO$_2$ and HC-SO$_3$ are increased compared to C-SO$_2$ and C-SO$_3$.

A further understanding of this invention can be had from the following nonlimiting examples. As used herein, unless expressly stated to the contrary, all temperatures and temperature ranges refer to the centigrade system and the terms ambient and room temperature refer to about 20°–25° C. The term percent or (%) refers to weight percent and the terms mole and moles refer to gram moles unless otherwise specified.

EXAMPLES

Example 1.

Materials

[3,3,3',3',4,4,4',4'-$^2$H$_8$]-homocystine was purchased from CDN Stable Isotopes (Montreal, Canada). [3,3,3',3'-$^2$H$_4$]-cystine was purchased from Cambridge Isotope Labs (Woburn, Mass.). HC-SO$_2$ and C-SO$_2$ were purchased from Tocris Neuramin (Bristol, U.K.). N-methyl-N-t-butyldimethylsilyl trifluoroacetamide (MTBSTFA) was purchased from Regis Chemical Company (Morton Grove, Ill.). Anion (AG-MP1) and cation (AG-MP-50) exchange resins were purchased from Bio-Rad laboratories (Richmond, Calif.). 30% hydrogen peroxide (H$_2$O$_2$) was from J. T. Baker Chemicals (Phillipsburg, N.J.). All other chemicals of the highest purity were purchased from Sigma Chemical Company (St. Louis, Mo.) or other commercial vendors. Serum separation tubes for collection of blood samples were purchased from Becton Dickinson (Franklin Lakes, N.J.).

Synthesis of [3,3,4,4-$^2$H$_4$]homocysteine sulfinic acid and [3,3,4,4-$^2$H$_4$]homocysteic acid DL-[3,3,4,4-$^2$H$_4$]HC-SO$_2$ was prepared from [3,3,3',3',4, 4,4',4'-$^2$H$_8$]homocystine by oxidation as described [Luchi and De Marco (1972) Anal. Biochem 45:236–241]. Briefly, to a solution of 2 mg (7.5 μmol) of [3,3,3',3',4,4,4',4'-$^2$H$_8$]homocystine in 200 μl of 0.1 N NaOH, 0.5 μmols of CuCl$_2$ was added and incubated at 37° C. for 3 hours. The solution was bubbled with air every 30 minutes. At the end of 3 hours, the solution was passed through a plastic column containing 150 mg of strong anion exchange resin (AG-MP1). The column was washed with 12 mL of water and eluted with 3 mL 4M acetic acid/1 N HCl, and dried in a vacuum centrifuge.

[3,3,4,4-$^2$H$_4$]HC-SO$_2$ was further oxidized with approximately 0.5 moles of KMnO$_4$ in HCl to 1 mole of [3,3,4,4-$^2$H$_4$]HC-SO$_3$. To a 12×75 mm borosilicate tube containing 1 mg (5.85 μmol) of dried [3,3,4,4-$^2$H$_4$]HC-SO$_2$ was added 3.10 μmols of KMnO$_4$ in 0.05N HCl (200 μL final volume). After 30 minutes at room temperature, the samples were centrifuged at 1500 G at room temperature for 10 minutes. The supernatants were collected because the supernatants had a faint pink color of unreduced KMnO$_4$, which interfered in subsequent steps. Small aliquots representing 2% of [3,3,4,4-$^2$H$_4$]HC-SO$_2$ were added sequentially until the supernatant was colorless (a total of 8%) and the A544 was less than 0.5% of the control KMnO$_4$ sample that did not contain any HC-SO$_2$. This maneuver ensured that less than a 2% excess of unoxidized [3,3,4,4-$^2$H$_4$]HC-SO$_2$ remained in the sample and, conversely, that greater than 98% of the total [3,3,4,4-$^2$H$_4$]HC-SO$_2$ was oxidized to [3,3-$^2$H$_2$]C-SO$_3$. Without wishing to be bound by any particular theory, the less than perfect stoichiometry of KMnO$_4$ oxidation presumably occurs because of varying amounts of reduced KMnO$_4$ contaminating even freshly prepared solutions of KMnO$_4$.

[3,3-$^2$H$_2$]cysteine sulfinic acid and [3,3-$^2$H$_2$]cysteic acid

A modification of the method of synthesis of HC-SO$_2$ was used to make C-SO$_2$. However, a large precipitate formed on addition of CuCl$_2$ to the solution of cystine, and alternative methods using cysteine as the starting material and the use of $H_2O_2$ were explored.

1.23 mg (10 μmol) of L-[3,3-$^2H_2$]cysteine was dissolved in 300 μL of 0.1N NaOH. To this solution, 300 nmol of $CuCl_2$ was added, mixed and incubated at 37° C. for 12 hours. At the end of incubation, 400 μl of 0.1N NaOH was added, mixed and passed through a plastic column containing 100 mg SAX resin. The resin was washed with 12 ml of water and [3,3-$^2H_2$]C-$SO_2$ was eluted with 1.8 ml of 1N HCl and dried in a vacuum centrifuge.

113 μl of 30% $H_2O_2$ (1 mmol) was added to a solution of 1.23 mg (10 μmol) of L-[3,3$^2H_2$]cysteine in 300 μL of 0.1 N NaOH, mixed and incubated at 37 ° C. At the end of the 30 minutes, 400 μL 0.1N NaOH was added to the mixture and the mixture was passed through a plastic column containing 100 mg SAX resin. The resin was washed with 12 ml of water and eluted with 1.8 ml of 1N HCl. The eluate containing [ 3,3$^2H_2$]C-$SO_3$ was dried down in a vacuum centrifuge.

The stable isotope labeled internal standards prepared in the laboratory were quantitated based on the ratio of [M-57]+ m/z of stable isotope labeled compound to [M-57]+ m/z of known quantities (based on weight) of native compounds.

Example 2

Human Sampling

Approval was obtained from Human Subjects Committee of the University of Colorado Health Sciences Center, Denver, Colo., for studies of blood from normal human subjects. Five mL samples of blood were drawn to serum separation tubes from each of 20 apparently normal individuals after an overnight fast. The blood samples were allowed to clot, the tubes were centrifuged at 1,500×g for 10 minutes and sera samples were poured into plastic tubes and stored at −20° C. until prepared for analysis.

IRB approval was obtained for use of blood, destined for discard in the clinical laboratory, from patients admitted to North Pavilion Psychiatric Hospital. Sera and anticoagulated whole blood collected from patients on the day of admission were analyzed for serum and red cell folates and serum oxidized sulfhydryl amino acids in a blinded fashion. Blood samples were given unique identification numbers, and the diagnoses for the corresponding patients were revealed after data analysis. Patient confidentiality was maintained at all times.

Example 3

Biological Sample Preparation 100 ng each of [3,3-$^2H_2$]-C-$SO_2$, [3,3-$^2H_2$]-C-$SO_3$, [3,3,4,4-$^2H_4$]-HC-$SO_2$ and [3,3,4,4-$^2H_4$]-HC-$SO_3$ were added to 100 μL of each human serum sample and each sample was then diluted to a final volume of 3 mL using 0.05 M $NH_4OH$. Each mixture of serum and stable isotope labeled-OSAA in $NH_4OH$ was passed through a 2 mL column containing 100 mg strong anion exchange resin (AG-MP1). The strong anion exchange resin, which binds all the compounds being measured, was washed with 12 mL of 0.05 M $NH_4OH$, followed by 12 mL of water, and then the oxidized SAAs were eluted with 1.4 mL of 1 N HCl. This eluate was passed through another 2 mL column containing 50 mg of strong cation exchange resin, e.g., AG-MP-50, which ensured further purification of the sample, and the effluent was collected in a 2 mL plastic vial. The strong cation exchange resin column was further washed with 400 μL of 1 N HCl, and the wash solution was combined with the effluent. The effluent was dried in a vacuum centrifuge. Derivatization was carried out as described below. The derivatized samples were transferred to autosampler vials before GC/MS analysis. Same methodology as for serum processing is employed for assay in other biological fluids such as urine or cerebrospinal fluid.

Example 4

Gas Chromatography/mass spectrometry

Derivatization before GC/MS analysis was achieved by incubation of each dried sample with a mixture of 15 μL MTBSTFA and 35 μL acetonitrile at 90° C. for 60 minutes.

Two μL of derivatized sample was injected onto the capillary column using an automatic falling needle injector. Gas chromatography was performed on a Hewlett-Packard 5890A gas chromatograph using helium as carrier through a 10 m by 0.25 mm (internal diameter) SPB-1 fused silica capillary column (Supelco, Belfont, Pa.). The column head pressure was 50 kPa. The injector port temperature was 250° C., and the initial column temperature was 80° C. A temperature ramp of 30° C./minute was applied to a final temperature of 300° C. Ionization was by electron impact. Mass spectrometry was performed using a Hewlett Packard 5971A mass detector. The electron multiplier was set at 1500 V for pure standards and at 1800 V for biological samples (e.g., serum). Spectra of standards were determined in the scan mode, and quantitation was carried out by selected ion monitoring Quantitation of SAA was based on the ratio of [M-57]$^+$ m/z of native compound to [M-57]$^+$ m/z of known quantities of stable isotope labeled compound using SIM (Stabler et al. (1987) supra; Deutsch, J. C. and Kolhouse, J. F. (1993) *Anal. Chem.* 65:321–326).

Selected Ion Monitoring

Quantitation of each SAA was based on the ratio of [M-57]$^+$ m/z of native compound to [M-57]$^+$ m/z of known quantities of stable isotope labelled compound using SIM (14,15). A SIM computer program was written to analyze all four sulfur amino acids and their corresponding stable isotope labelled internal standards following a single injection of 2 μL of derivatized sample. The [M-57]$^+$ ions for each of the SAA (Table 1) were monitored from 5.5' to 7.5' with a dwell time of 10 ms for each compound.

It was necessary to correct peak areas, determined by computer integration, for naturally occurring isotopes. There was a 21% abundance of m/z 440 when a sample of pure, unlabeled C-$SO_2$ ([M-57]$^+$= m/z 338) was analyzed by GC/MS. Similar corrections for the ions used in the respective isotope dilution assays were 18% for C-$SO_3$, 1.6% for HC-$SO_2$ and 0.5% for HC-$SO_3$. The contributions of the stable isotope labelled SAA to the monitored ions of the native compounds were less than 0.5% and no corrections were applied. For example, the following formula was used for quantitation of C-$SO_2$ from 100 μL of serum:

$$CSO_2 \text{ (ng/ml)} = \{A/[B-(A * 0.21)]\} * 10\ C$$

where A is the isotopic abundance of ion m/z 438, B is the isotopic abundance of ion m/z 440 and C is the quantity in ng of [3,3-$^2H_2$]C-$SO_2$ added at the outset of sample preparation While various embodiments of the present invention have been described in detail, it is apparent that modifications and adaptations will occur to those skilled in the art. However, it is to be expressly understood that such modifications and adaptations are within the spirit and scope of the present invention, as set forth in the following claims.

We claim:

1. A method for determination of in vivo concentration in a body fluid of one or more endogenous oxidized sulfhydryl amino acids selected from the group consisting of cysteine sulfinic acid, cysteic acid, homocysteine sulfinic acid and homocysteic acid, said method comprising the steps of:

(a) combining a known mount of at least one internal standard oxidized sulfhydryl amino acid selected from the group consisting of deuterated cysteine sulfinic acid, deuterated cysteic acid, deuterated homocysteine sulfinic acid and deuterated homocysteic acid, with a body fluid collected in vitro, said body fluid comprising at least one of said endogenous oxidized sulfhydryl amino acids;

(b) at least partially purifying said endogenous and internal standard deuterated oxidized sulfhydryl amino acids from other components in said in vitro body fluid;

(c) quantitating said endogenous oxidized sulfhydryl amino acid concentrations in said purified in vitro body fluid of step (b) by gas chromatography/mass spectrometry analysis;

(d) quantitating said internal standard deuterated oxidized sulfhydryl amino acid concentration in said purified in vitro body fluid of step (b) by gas chromatography/mass spectrometry analysis and determining the losses in said internal standard deuterated oxidized sulfhydryl amino acids; and (e) determining the in vivo concentrations of said endogenous oxidized sulfhydryl amino acid(s) by correcting the quantitated in vitro endogenous concentrations for losses in said known amounts of the internal standard oxidized deuterated sulfhydryl amino acids.

2. A method for determination of in vivo concentration in a body fluid of one or more endogenous oxidized sulfhydryl amino acids selected from the group consisting of cysteine sulfinic acid, cysteic acid, homocysteine sulfinic acid and homocysteic acid, said method comprising the steps of:

(a) combining a known amount of at least one internal standard oxidized sulfhydryl amino acid selected from the group consisting of $[3,3\text{-}^2H_2]$ cysteine sulfinic acid, $[3,3\text{-}^2H_2]$ cysteic acid, $[3,3,4,4\text{-}^2H_4]$ homocysteine sulfinic acid and $[3,3,4,4\text{-}^2H_4]$ homocysteic acid, with a body fluid collected in vitro, said body fluid comprising at least one of said endogenous oxidized sulfhydryl amino acids;

(b) at least partially purifying said endogenous and internal standard deuterated oxidized sulfhydryl amino acids from other components in said in vitro body fluid;

(c) quantitating said endogenous oxidized sulfhydryl amino acid concentrations in said purified in vitro body fluid of step (b) by gas chromatography/mass spectrometry analysis;

(d) quantitating said internal standard deuterated oxidized sulfhydryl amino acid concentration in said purified in vitro body fluid of step (b) by gas chromatography/mass spectrometry analysis and determining the losses in said internal standard deuterated oxidized sulfhydryl amino acids; and (e) determining the in vivo concentrations of said endogenous oxidized sulfhydryl amino acid(s) by correcting the quantitated in vitro endogenous concentrations for losses in said known amounts of the internal standard oxidized deuterated sulfhydryl amino acids.

3. The method of claim 2 wherein the purified endogenous and internal standard oxidized sulfhydryl amino acid(s) are derivatized prior to gas chromatography analysis.

4. The method of claim 3, wherein the derivatizing agent is N-methyl-N-t-butyldimethylsilyl trifluoroacetamide.

5. The method of claim 2 wherein the body fluid is selected from the group of serum, plasma, cerebrospinal fluid, urine, saliva, semen, pleural fluid, peritoneal fluid and amniotic fluid.

6. The method of claim 2 wherein the partial purification step (b) comprises the steps of:

(a) chromatography using a strong anion exchange resin; and (b) chromatography using a strong cation exchange resin.

7. The method of claim 6 wherein said body fluid is selected from the group consisting of serum, urine, semen, saliva, pleural fluid, peritoneal fluid, amniotic fluid and cerebrospinal fluid.

* * * * *

UNITED STATES PATENT AND TRADEMARK OFFICE
CERTIFICATE OF CORRECTION

PATENT NO. : 5,559,038

DATED : Sep. 24, 1996

INVENTOR(S) : Kolhouse et al.

It is certified that error appears in the above-indentified patent and that said Letters Patent is hereby corrected as shown below:

At col. 4, line 36, "[3,3-$^{2H}_2$] cysteine" should read --[3,3-$^2$H$_2$] cysteine--.

At col. 7, line 14, "0,994" should read --0.994--.

At col. 14, line 31, "monitoring," should be followed by --(SIM).--.

At col. 14, line 65, "ration" should read --ration.--.

Signed and Sealed this

Seventh Day of January, 1997

Attest:

BRUCE LEHMAN

*Attesting Officer*    *Commissioner of Patents and Trademarks*